(12) United States Patent
Chang et al.

(10) Patent No.: US 7,147,606 B1
(45) Date of Patent: Dec. 12, 2006

(54) URINARY DIAGNOSTIC SYSTEM HAVING A RETRIEVABLE SENSING DEVICE

(76) Inventors: T. Debuene Chang, P.O. Box 1156, Danville, CA (US) 94526; Luiz B. Da Silva, 1995 Camino Ramon Pl., Danville, CA (US) 94526; Victor C. Esch, 5808 Canyon Vista Dr., Albuquerque, NM (US) 87111

( * ) Notice: Subject to any disclaimer, the term of this patent is extended or adjusted under 35 U.S.C. 154(b) by 406 days.

(21) Appl. No.: 10/673,916

(22) Filed: Sep. 26, 2003

Related U.S. Application Data

(60) Provisional application No. 60/414,116, filed on Sep. 27, 2002.

(51) Int. Cl.
*A61B 5/00* (2006.01)

(52) U.S. Cl. ..................................... 600/561

(58) Field of Classification Search ............ 600/29–32, 600/486, 561
See application file for complete search history.

(56) References Cited

U.S. PATENT DOCUMENTS

| | | | |
|---|---|---|---|
| 4,846,191 A * | 7/1989 | Brockway et al. .......... 600/561 |
| 5,303,026 A | 4/1994 | Strobl et al. ................ 356/318 |
| 5,433,216 A | 7/1995 | Sugrue et al. ............... 128/778 |
| 5,704,353 A * | 1/1998 | Kalb et al. ................... 600/342 |
| 6,159,156 A * | 12/2000 | Van Bockel ................ 600/485 |
| 6,293,923 B1 * | 9/2001 | Yachia et al. ............. 604/96.01 |
| 6,334,064 B1 | 12/2001 | Fiddian-Green ............ 600/311 |
| 6,398,718 B1 * | 6/2002 | Yachia et al. ................. 600/29 |
| 6,442,413 B1 * | 8/2002 | Silver .......................... 600/345 |
| 6,682,473 B1 * | 1/2004 | Matsuura et al. ............. 600/29 |
| 6,682,490 B1 * | 1/2004 | Roy et al. .................... 600/486 |
| 6,746,421 B1 * | 6/2004 | Yachia et al. ............. 604/93.01 |
| 2002/0138009 A1 * | 9/2002 | Brockway et al. .......... 600/485 |
| 2003/0136417 A1 * | 7/2003 | Fonseca et al. ............. 128/899 |

* cited by examiner

*Primary Examiner*—Max F. Hindenburg
*Assistant Examiner*—Michael Apanius
(74) *Attorney, Agent, or Firm*—Nicole E. Coppes-Gathy

(57) ABSTRACT

A diagnostic system is disclosed. The diagnostic system comprises a sensing device having a retrieval wire. The sensing device is configured to collect data. The system also includes a deployable housing that has a body defining an interior and an exterior. The housing is configured to allow fluid to flow through the housing and the housing completely encloses the sensing device. The system also includes a disposer for disposing the housing into a body part. The system also includes a processing device configured to receive the data from the sensing device. The processing device is configured to transmit the data.

8 Claims, 12 Drawing Sheets

URINARY DIAGNOSTIC SYSTEM HAVING A RETRIEVABLE SENSING DEVICE

PRIORITY CLAIM

This application claims priority to U.S. Patent Application Ser. No. 60/414,116, filed Sep. 27, 2002.

BACKGROUND

The present invention relates to a medical device and system that can be used to evaluate bladder pressure in patients.

Abnormal urinary voiding patterns are very common worldwide, affecting both women and men. Just for incontinence alone, the World Health Organization estimates that there are 200 million men and women worldwide with symptoms of urinary incontinence. This condition affects the patient both physically and emotionally—affecting the patient's quality of life. It is predicted that urinary incontinence will affect an estimated 30 million American women of all ages. This condition can interfere with work, travel, recreation and sexual activities. Urinary incontinence is also associated with urinary tract infections, and scrotal, perineal, and labial ulcers. Male incontinence is most commonly caused by prostate enlargement and/or surgery. Female incontinence often results from stretching of the pelvic support structures during pregnancy and childbirth. Additional contributory factors include a history of hysterectomy and post menopause.

In both sexes, other contributing factors to urinary incontinence include obesity, cigarette smoking, pelvic radiation therapy, diabetes, Parkinson's disease, back injury, cerebral vascular accident, and dementia. There are a variety of treatment options for bladder control problems ranging from behavioral therapy, pelvic muscle exercises, biofeedback, bladder training, fluid/dietary modifications, medications, urethral devices, pelvic floor supporters, and surgical procedures, such as bladder suspensions, slings, and urethral bulking procedures. In relatively minor cases, satisfactory treatment may include the use of absorbent pads combined with strengthening exercises and behavior modification. Anti-spasmodic medications may be added to the multi-modality regimen for treatment. Surgery may become necessary if these combinations of non-invasive treatments are inadequate. Various numbers of surgical options are currently available with many surgeries reinforcing and supporting the bladder neck region, either with anterior suture support or posterior anchored suture or sling support. Other procedures available include surgical injections of urethral bulking materials or elements that mechanically close the urethral opening (i.e., inflatable balloons, clamps).

A significant number of people also suffer from urinary retention. Retention in men is primarily caused by enlarged prostate (benign prostatic hypertrophy) or prostate carcinoma. Urinary retention in women is subtler to diagnose and maybe a result of weak bladder muscles in the elderly population.

Many abnormal voiding patterns are much more complicated than incontinence or retention alone. These people suffer from a mixed picture of both incontinence and retention in various degrees.

In order to determine effective therapy for these various, abnormal, voiding patterns of incontinence and retention, a variety of diagnostics are now performed to measure the bladder pressure during bladder filling and voiding. These devices are commonly catheter-based systems that are inserted into the bladder and remain in place during the measurement (e.g., U.S. Pat. No. 5,433,216 to Sugrue et al. and U.S. Pat. No. 6,334,064 to Fiddian-Green et al.). The disadvantage of these catheter-based systems is that the patient is forced to undergo tests in a clinical setting. In addition, the large catheter size can lead to patient discomfort during the measurement. Patients are immobilized during the test since they are physically attached to the equipment and machinery.

Improving these diagnostic techniques can greatly improve effective treatment of the above-referenced bladder conditions. It is often difficult to obtain pressure readings under normal conditions using the currently available pressure sensing catheters. Given the limitations of current techniques to diagnose urinary problems, there is a need for a novel device, system and method that can simplify and improve the accuracy for diagnosis and treatment of urinary problems.

SUMMARY

A diagnostic system is disclosed. The diagnostic system comprises a sensing device having a retrieval wire. The sensing device is configured to collect data. The system also includes a deployable housing that has a body defining an interior and an exterior. The housing is configured to allow fluid to flow through the housing and the housing completely encloses the sensing device. The system also includes a disposer for disposing the housing into a body part. The system also includes a processing device configured to receive the data from the sensing device. The processing device is configured to transmit the data.

An alternative embodiment of the diagnostic system is also disclosed. The diagnostic system comprises a sensing device having a retrieval wire. The sensing device is configured to collect data. The system also includes a deployable housing that has a body defining an interior and an exterior. The housing is configured to allow fluid to flow through the housing and the housing completely encloses the sensing device. The system also includes a disposer for disposing the housing into a body part.

A method for using a sensing device disposed in a body part having an interior is disclosed. The method comprises disposing the sensing device having a retrieval wire into a deployable housing. The housing has a body defining an interior and an exterior. The housing is configured to allow fluid to flow through the housing to the sensing device. The housing completely encloses the sensing device. The housing enclosing the sensing device is compressed into an interior of a first sheath. A push bar is disposed into the interior of the first sheath proximate the housing. The first sheath is inserted into the body part of a body. The push bar is operated to dispose the housing enclosing the sensing device into the interior of the body part. The first sheath is removed from the body part with the retrieval wire exiting the interior of the body part. Data is collected using the sensing device and transmitted from the sensing device to a processing device. The retrieval wire of the sensing device is located and inserted through an interior of a second sheath. The second sheath is inserted into the interior of the body part. The second sheath is configured to receive the housing enclosing the sensing device. The housing and the sensing device are retracted into the interior of the second sheath using the retrieval wire. The second sheath is removed from the body part.

BRIEF DESCRIPTION OF THE DRAWINGS

Referring now to the figures, wherein like elements are numbered alike.

DETAILED DESCRIPTION

Those of ordinary skill in the art will realize that the following description is illustrative only and not in any way limiting. Other embodiments will readily suggest themselves to such skilled persons.

Figure 1A:
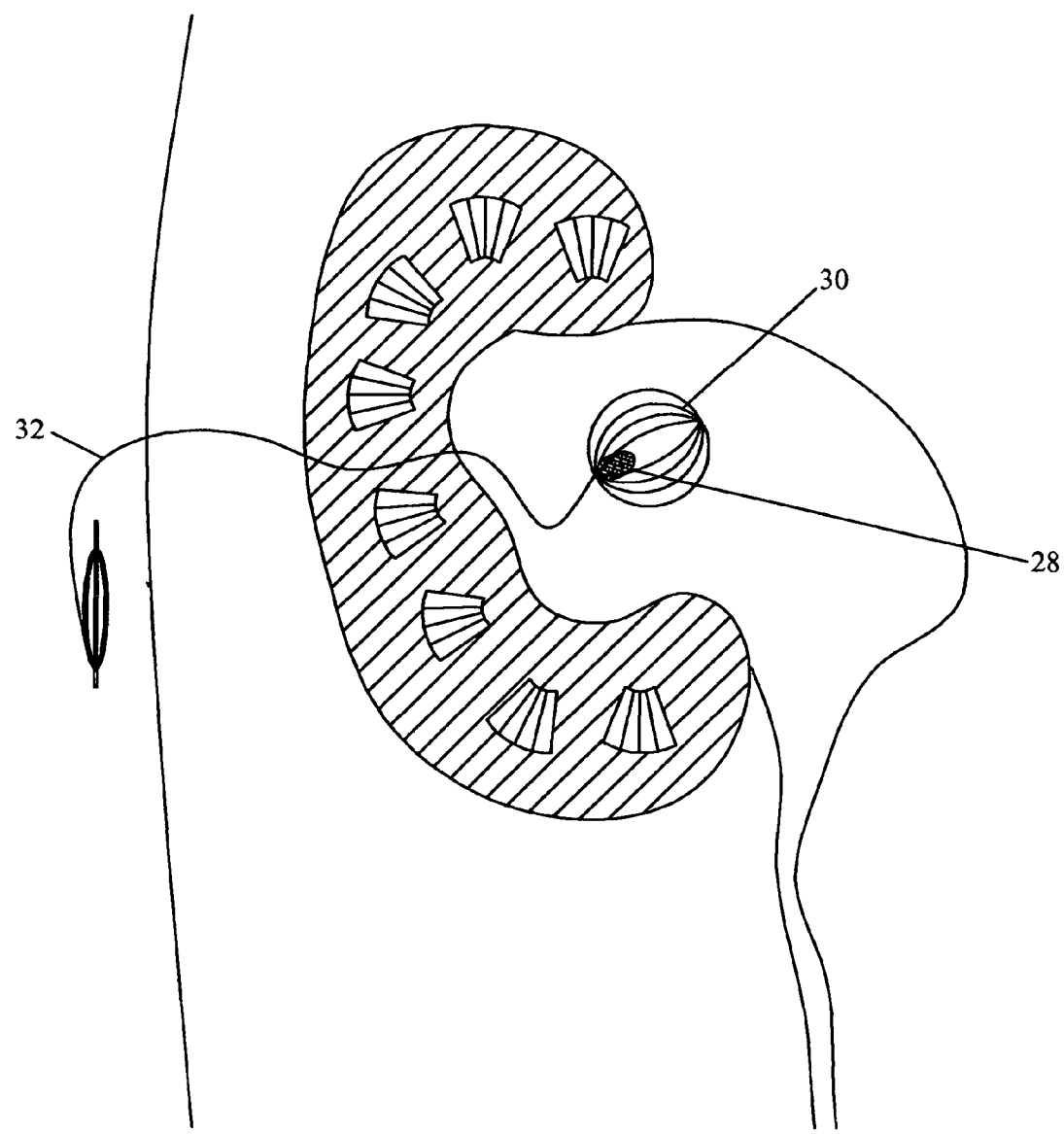
FIG. 1A is an anatomical cross section illustrating one of the kidneys.

The sensing device and system of the present invention can be utilized in any body part (i.e., generally human, although use in animals is contemplated) that can safely house the sensing device for collecting measurements. FIG. 1A illustrates an anatomical cross section of a kidney (i.e., a diseased kidney is illustrated) with the sensing device being deposited therein. For ease in describing the present invention, the sensing device and system will be described in relation to depositing the sensing device in the bladder, although other body parts are contemplated.

Figure 1B:
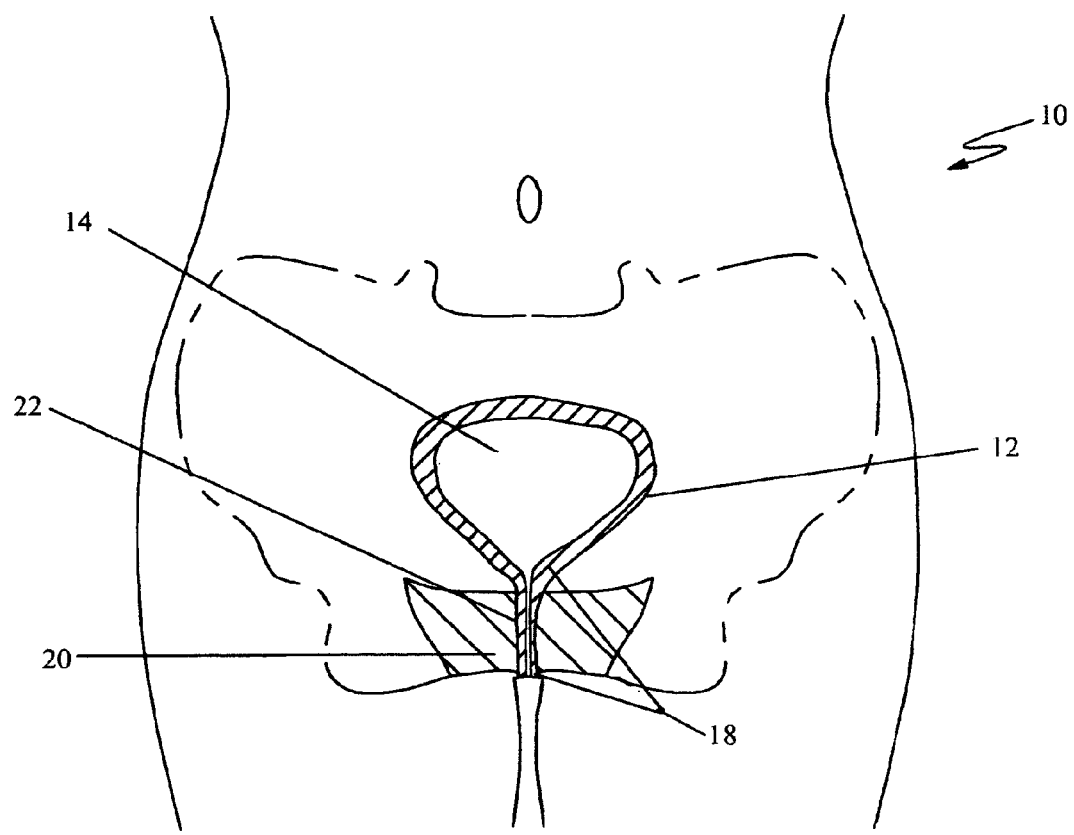
FIG. 1B is an anatomical cross section illustrating the bladder and urethra.

FIG. 1B illustrates an anatomical cross section of the bladder and urinary tract 10. The bladder 12 expands and dilates as urine 14 fills the bladder. In a normal patient, voiding is accomplished by contraction of the bladder muscles 16 orchestrated in tandem with a relaxation of the sphincteric muscles 18 of the bladder neck and pelvic support muscles 20 that allows urine 14 to flow out through the urethra 22. For patients with urinary incontinence, leaking of urine can occur during normal daily function. In order to determine the cause of incontinence, the correlation of leaking of urine with bladder pressure is an important measurement.

Figure 2:
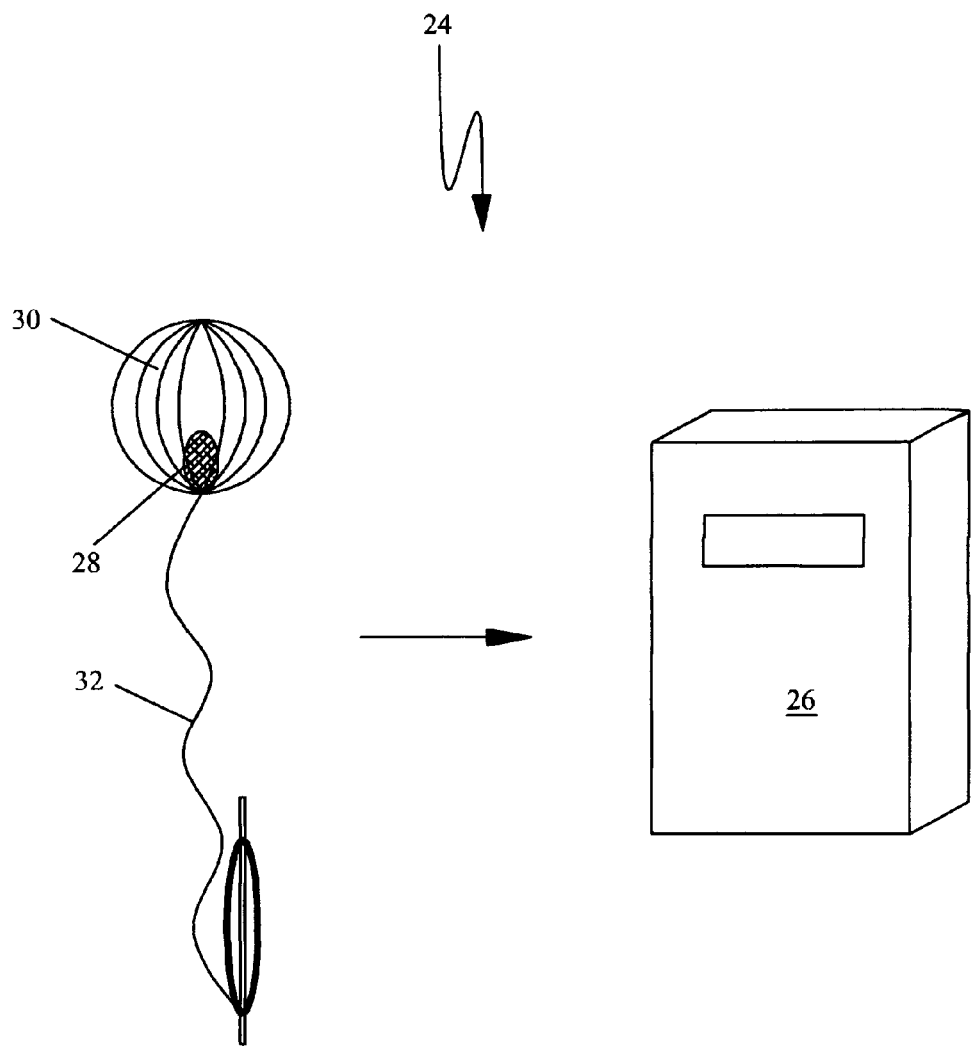
FIG. 2 illustrates an embodiment of the system and how it would be used in accordance with the present invention.

FIG. 2 illustrates a first embodiment of a urinary diagnostic system 24. The system 24 includes a processing device 26 that receives and records signals generated by sensing device 28. In this embodiment, transfer of the measurement is by radio frequency, although other methods are contemplated. The sensing device 28 includes a sensing element (See FIG. 3) that detects changes in pressure and a transmitter or transceiver system (See FIG. 3) for communicating measurements to the processing device 26. A suitable sensing device includes, but is not limited to, thermal sensing devices, conductive sensing devices, capacitive sensing devices, inductive sensing devices, resistive sensing devices, optical pressure sensing devices, and the like. Any of these sensing devices can be easily integrated into a thin (i.e., less than about 0.5 mm) assembly.

The sensing device 28 is contained within a housing (or cage) 30 that expands when the sensing device 28 is released into the bladder (not shown). The housing 30 can made of a material that is flexible to allow for the expansion function, such as a polymer, polytetrafluoroethylene or Teflon®, non-dissolvable biocompatible materials, polyurethane, polyethylene, latex, and the like, or a metal material, such as titanium, copper, gold, surgical steel, polytetrafluoroethylene or Teflon®-coated metal, and the like. The housing 30 prevents the sensing device 28 from being ejected during bladder voiding.

In alternative embodiment, the housing is comprised of a material that will, after a time, decompose in the bladder when exposed to urine. Examples of the material include natural collagen, plain gut, polyglactin 910, polydioxanone, collagen, polyglyconate, polyglycolic acid, and the like. After the housing 30 dissolves, the sensing device 28 can pass through the bladder and urethra to the outside of the body.

In an alternative embodiment, the sensing device 28 is not surrounded by an expanding housing 30. This embodiment is usually used in the doctor's office, hospital, clinic, or similar setting when multiple voiding is not planned and the risk of the sensing device being ejected from the bladder is small.

The sensing device 28 has a retrieval wire 32. In one embodiment, the retrieval wire 32 includes an antenna (See FIG. 3) that is used by the sensing device 28 to transmit measurements to the processing device 26. The retrieval wire 32 comprises a conductive material that can function as an RF antenna and has a tensile strength sufficient for retrieval of the sensing device from the bladder. Examples include, but are not limited to, copper, gold, aluminum, titanium, surgical steel, and the like. In another embodiment, the retrieval wire 32 includes a urine sensing device (not shown) that can detect flow (or leaking) of urine due to incontinence.

Figure 13:
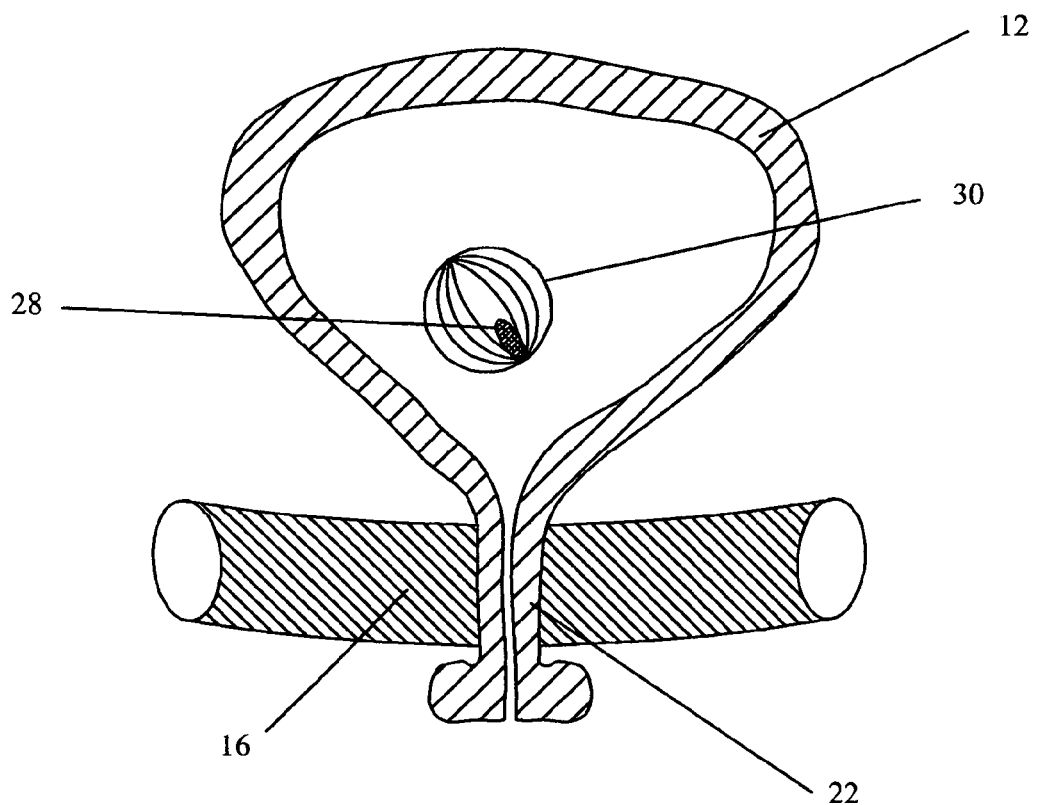
FIG. 13 illustrates a sensing device, without a retrieval wire, disposed in the bladder.

In one embodiment, as illustrated in FIG. 13, the sensing device 28 does not have a retrieval wire 32. In the embodiment in which the housing 30 is comprised of a material that decomposes in the body, a retrieval wire 32 is not needed. The housing 30 will decompose and the sensing device 28 will pass through the system out of the body. In this case, no retrieval wire 32 is required, since the body will automatically dispose of the sensing device 28 during voiding.

Figure 3:
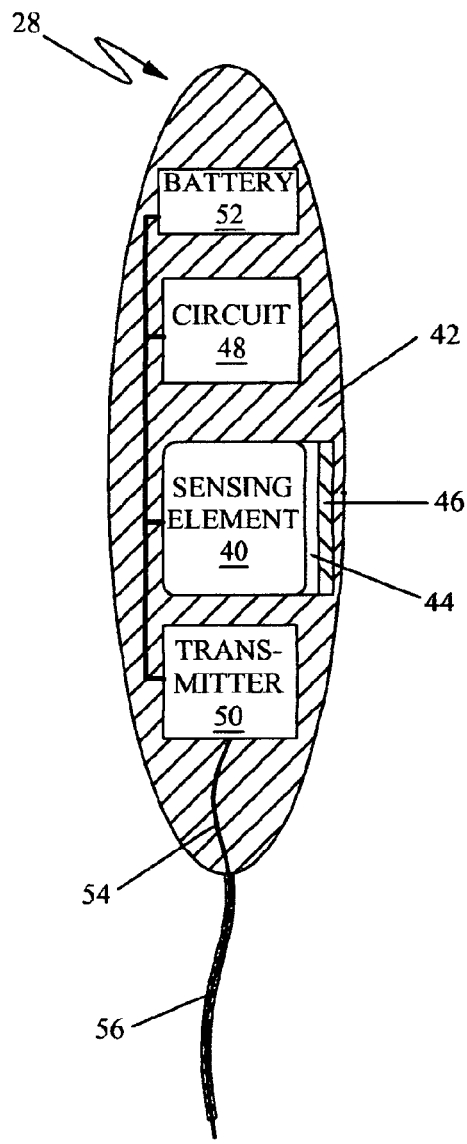
FIG. 3 shows a cross sectional view of an embodiment of the pressure sensing device.

In one embodiment of the sensing device 28, a battery (See FIG. 3) powers both the sensing element (See FIG. 3) and the RF transmitter (See FIG. 3). The measurements can be communicated to the processing device 26 using any commonly used RF techniques (e.g., amplitude modulation (AM) or frequency modulation (FM)).

In an alternative embodiment, the sensing device 28 is a passive sensing device that contains an inductive element (L) and a capacitive element (C) that forms a LC circuit whose RF changes with pressure. The RF is measured by the processing device 26 using commonly known impedance techniques. The advantages of using a passive sensing device are that this sensing device eliminates the need for a battery. The disadvantages are that the processing device 26 of the diagnostic system is more susceptible to noise, and therefore, the size of the processing device 26 needs to be larger to compensate FIG. 3 illustrates a cross section of the sensing device 28, in which the sensing device 28 is a pressure sensing device.

A pressure sensing element 40 is disposed within the interior 42 of the sensing device 28 with the active region 44 coupled to a deformable segment 46 that moves under external fluid pressure. The deformable segment 46 can be comprised of a latex material, polyurethane, biocompatible polymer, a polytetrafluoroethylene or Teflon®-coated metal, and the like. The pressure sensing element 40 can be any suitable pressure sensing device; a preferred example is the pressure sensing devices available from Integrated Sensing Systems (ISSYS). In a preferred embodiment, the sensing element 40 is a capacitive element whose capacitance changes under pressure. The sensing element 40 is connected to circuit 48. Circuit 48 generates signals from the measurements that the RF transmitter 50 transmits to the processing device 26. The RF transmitter 50 can use any FCC approved modulation and frequency. A battery 52 powers the circuit 48 and transmitter 50. The transmitter 50 connects to the antenna wire 54 that is encapsulated within a biocompatible polymer 56. In this embodiment, the processing device 26 detects the RF signal and demodulates the signal to determine the current pressure. The processing device 26 can collect measurements at a rate (e.g., about 1 Hz) selected by the user and record the data in an internal (or external) memory. The measurements can be immediately transferred, or saved for later transfer, to a computer or other appropriate device.

Figure 4:
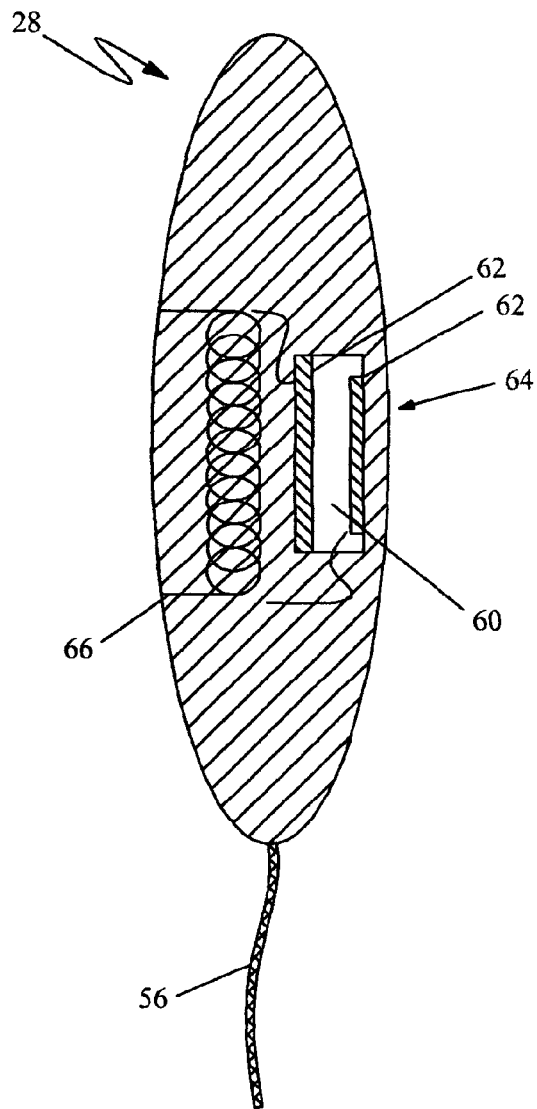
FIG. 4 shows a cross sectional view of an embodiment of the pressure sensing device that is passive.

FIG. 4 illustrates a cross section of the sensing device 28, in which the sensing device 28 is a passive sensing device. In this embodiment, the pressure-sensing element 60 is a parallel plate capacitor with at least two plates 62 attached to at least one flexible segment 64. The pressure-sensing element 60 is connected to an inductor 66 that can also act as the antenna for sensing device 28. In this embodiment, the RF of the sensing device is calculated by:

$$\omega = 1/\sqrt{LC}$$

Where:
ω is the radio frequency
L is the effective inductance
C is the effective capacitance In this embodiment, the processing device 26 measures the effective coupling between the external antenna 32 and the sensing device 28 as a function of frequency to determine the RF (i.e., RF illumination) of the sensing device 28.

Figure 5:
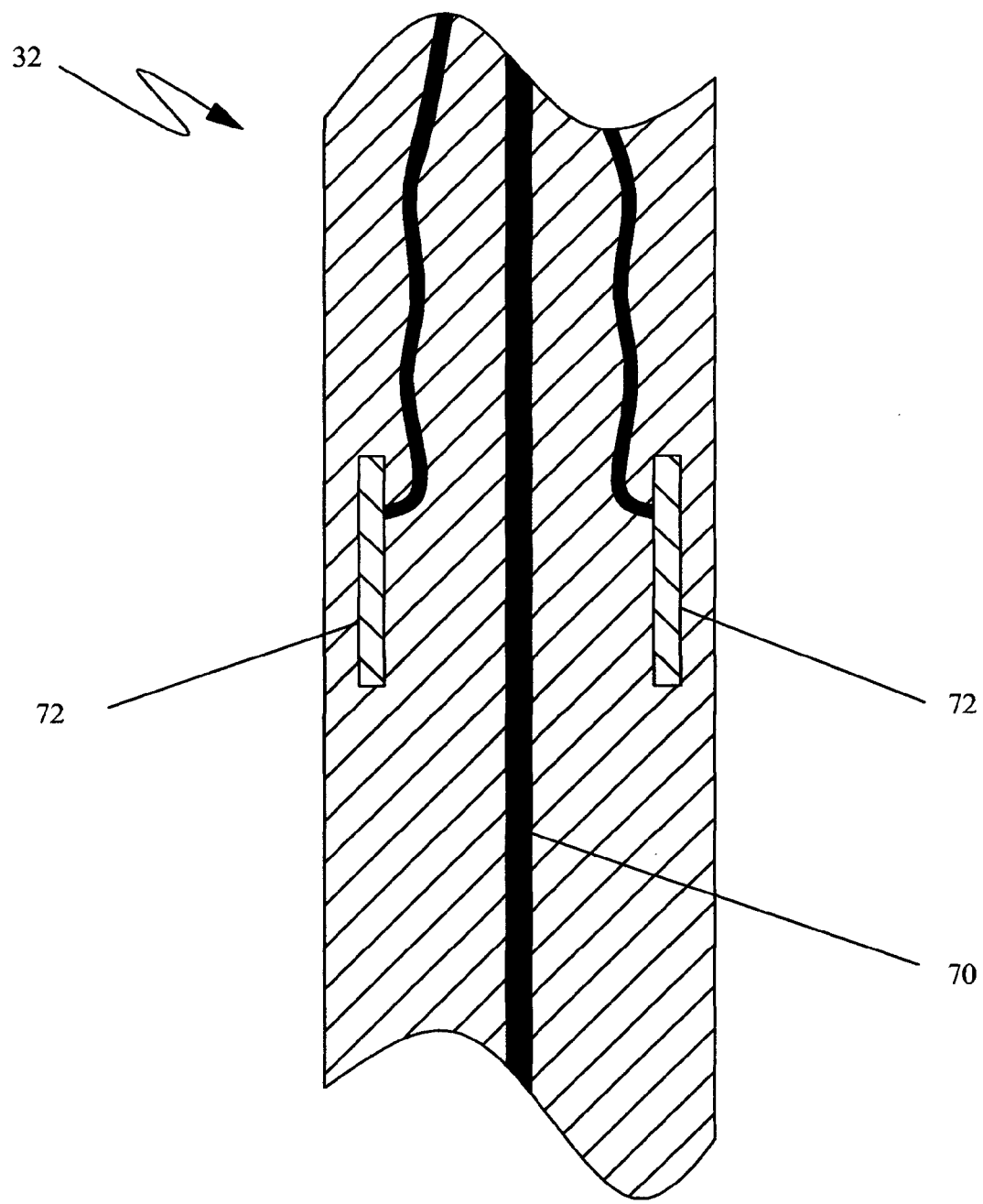
FIG. 5 shows a cross-sectional view of the retrieval wire that includes an antenna and urine flow sensing device.

FIG. 5 illustrates a cross section of the retrieval wire 32 having a multi-wire assembly that includes an antenna conductor 70 and electrodes 72 used by the processing device 28 to detect urine flow. As urine flows past the electrodes 72, the change in capacitance (and/or resistance) can be detected. In a preferred embodiment, a hydrophobic biocompatible polymer encapsulates the antenna conductor 70. The electrodes 72 are also encapsulated by the hydrophobic biocompatible polymer in order to reduce the risk of false readings due to trapped urine. Other materials for encapsulating the electrodes include, but are not limited to, polyethylene, polyurethane, polytetrafluoroethylene or Teflon®, and the like. In this multi-sensing device embodiment, the processing device 26 acquires the change in capacitance (and/or resistance) measurements continuously. The multi-sensing device measurements can be time multiplexed or frequency multiplexed by the sensing device electronics.

In another embodiment, an alternative sensing device that measures physiologically relevant parameters replaces the pressure sensing device. For example, the sensing device can be a chemical sensing device that measures urine chemistry during normal function. Such chemical sensing devices can measure potassium, sodium, protein, calcium and, possibly, pH. Other contemplated sensing devices could measure perfusion of the bladder wall, blood volume perfusion, oxygen perfusion, nitric oxide concentrations, carbon dioxide concentrations, and the like.

Figure 6:
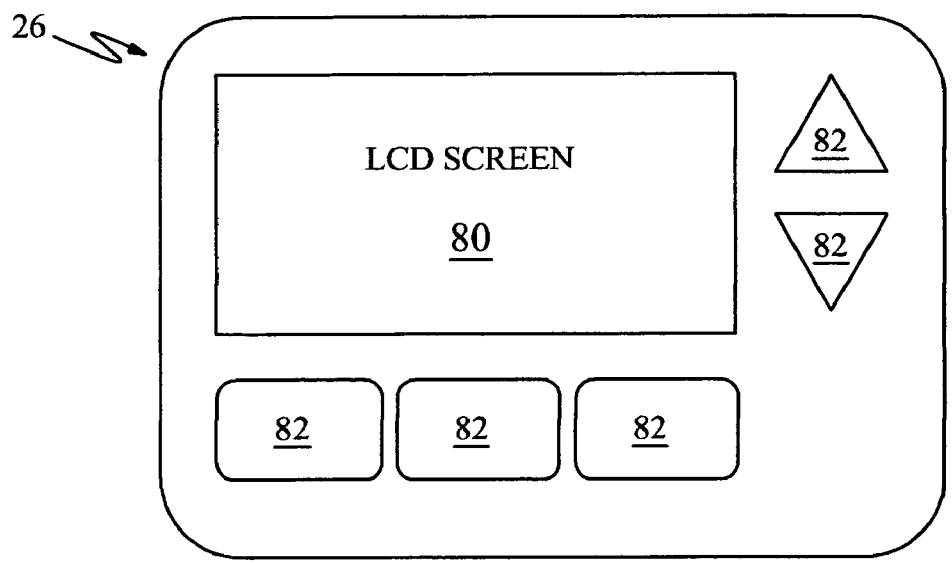
FIG. 6 is an illustration of one embodiment of the outside of the external receiver.

FIG. 6 is an illustration of an embodiment of the exterior of the processing device 26. The processing device 26 can include an LCD screen 80 and user interface controls (or buttons) 82. Generally, the user interface controls 82 should be intuitively simple for the patients to use. The patient activates and controls operation of the processing device 26 by operating user interface controls 82. In other embodiments, the processing device 26 can be programmed externally either using a cable connection or by wireless transmission. User controlled functions 82 include frequency of measurements, alarm levels, and method of signaling an alarm (i.e., either vibration or acoustic signal). The LCD screen 80 can display status, control menus, current sensing device readings, battery power, current time, time left for the sensing device to be in place, and the like. The processing device 26 can be adapted to record unusual events, such as exercise, coughing spells, sleeping, etc., which can be utilized in the analysis of the data.

The processing device 26 can be battery-powered or powered electronically. A portable battery-powered processing device 26 is desired for carrying by the user in a pocket or attached to the waistband in a similar fashion as pagers and cell phones. In the preferred embodiment, the processing device 26 is small enough (i.e., typically less than about 100 cm$^3$) to be easily carried by the patient during normal daily activity. The processing device 26 can include a clip similar to that used for pagers and cell phones for attaching the device to a waist belt. Alternative methods for carrying the processing device 26 include use of straps, a carrying case, a necklace design, and any other known methods of carrying a small portable device.

The alarm function of the processing device 26 can provide the user with feedback about excessive bladder pressure or a leak of urine. Biofeedback is an effective tool in treating incontinence. Data stored in the receiver can be transferred to a separate unit for printing and analysis. The data transfer can be by direct electrical cable connection (e.g., USB interface) or wireless communication (e.g. BLUETOOTH® standard).

Figure 7:
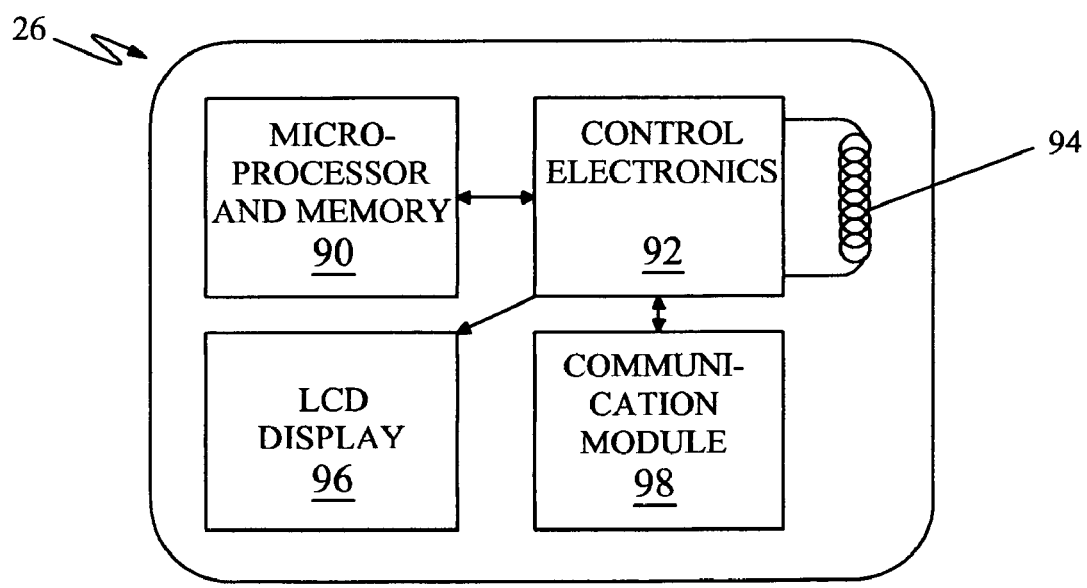
FIG. 7 is a block diagram of the key components of the external receiver.

FIG. 7 illustrates a block diagram of the key components of the processing device 26. A processing unit and memory 90 control operation of the sensing device 28. The processing unit can be a processor, a microprocessor, or any combination thereof. Input/output (I/O) devices (or control electronics) 92 receives user input and controls data acquisition and transfer. The I/O device 92 receives sensing device information through antenna 94 and converts the measurement to a pressure reading. The I/O device 92 also comprises an analog/digital converter (not shown) that can digitize the pressure reading. In a sensing device embodiment with an integrated urine flow sensing device, the I/O device 92 can also acquire the urine flow sensing device measurement. The processing unit 90 analyzes the digitized data and displays readings on the LCD screen 96. Measured data can be stored in memory 90 at a user specified rate (e.g., about 1 reading per second). The memory size should be large enough to store at least about 24 hours of readings. Patient input to the processing unit 90 is used to control operation and specify alarm conditions. The user can command the processing device 26 to transmit (i.e., by uploading information by external connection to a separate unit, depressing a "send" button to transmit, etc.) a log of all sensing device measurements collected during the day using the communication module 98. The communication module 98 can communicate with a separate unit (e.g., a desktop unit) using a cable or wireless communication.

In normal use, the sensing device is disposed (or inserted) into the bladder using a sheath and a hollow push rod (or trocar) mechanism. The sheath with the collapsed sensing device at the proximal end is guided into the bladder through the urethra. The wire attached to the device passes through the lumen of the push rod and exits the distal end of the sheath. Once the unit is in the bladder, the push rod is used to push the device out of the distal end of the catheter. As the device exits the distal end, the housing expands to a size that prevents the sensing device from being ejected through the urethra during normal bladder voiding. The catheter and push rod can now be removed, leaving the bladder sensing device in position within the bladder with its attached retrieval wire exiting the urethra.

Figure 8:
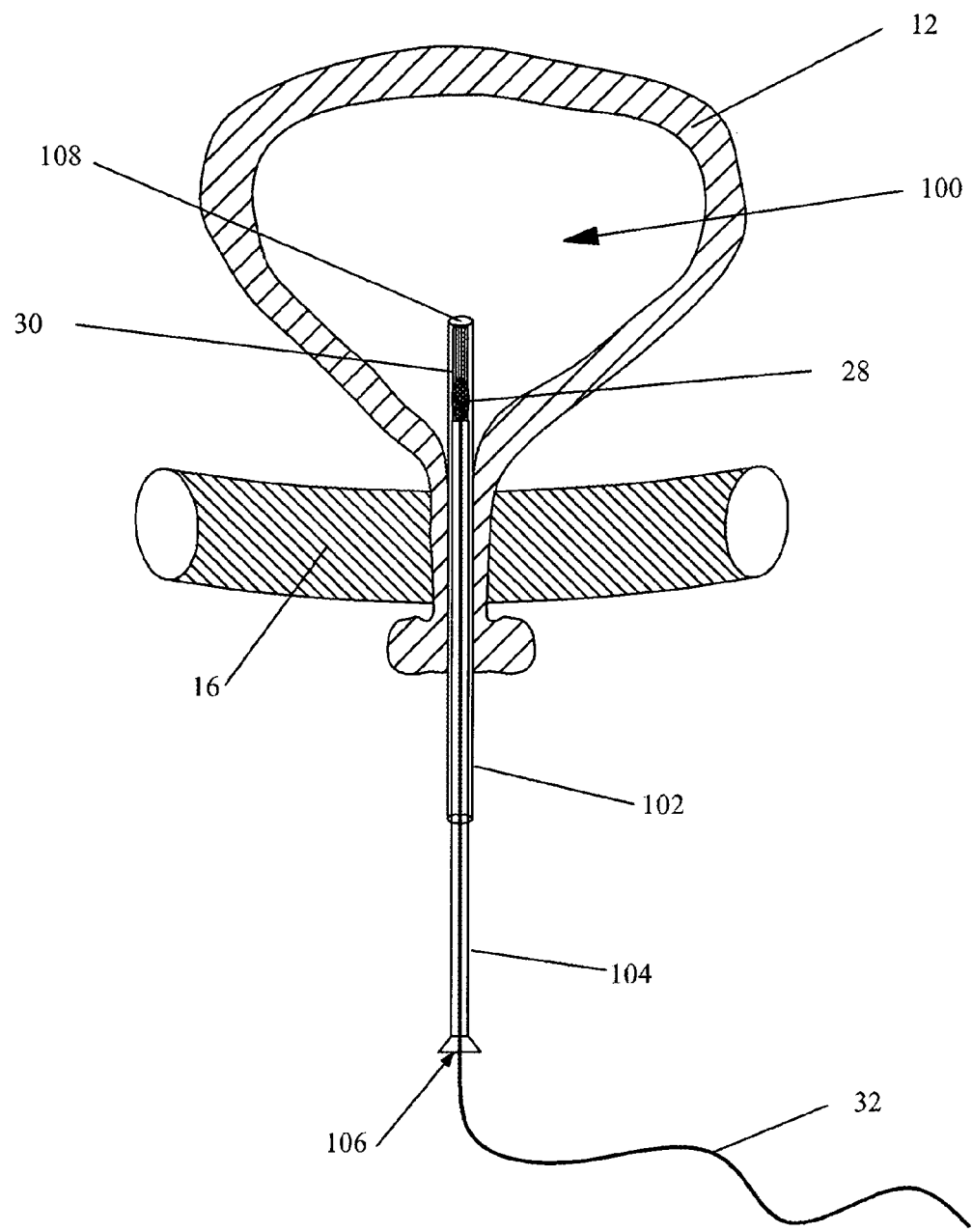
FIGS. 8, 9, and 10 illustrate the disposal of a sensing device into the bladder using a catheter.

FIG. 8 illustrates the sensing device 28 that is prepared for delivery 100 in the bladder 12. A mechanism (or disposer or catheter-type device) is utilized to dispose the sensing device 28 into the bladder 12. The sensing device 28 and the housing 30 are enclosed within a flexible sheath 102 that has been inserted into the urethra 22. The sheath 102 has forced the housing 30 into a closed configuration that minimizes the diameter of the sensing device 28. A hollow push rod or (trocar mechanism) 104 is positioned distal to the sensing device 28 with the retrieval wire 32 contained within the rod lumen (or interior) 106. The hollow push rod 104 can be manufactured of any biocompatible material such as polyethylene, polyurethane, steel, polytetrafluoroethylene or Teflon®, and the like. In normal use, the sheath 102 is inserted into the urethra 22 and the distal tip 108 of the sheath 102 is positioned within the bladder 12. The user can easily detect, by tactile feedback, when the distal tip 108 of the sheath 102 enters the bladder 12.

Figure 9:
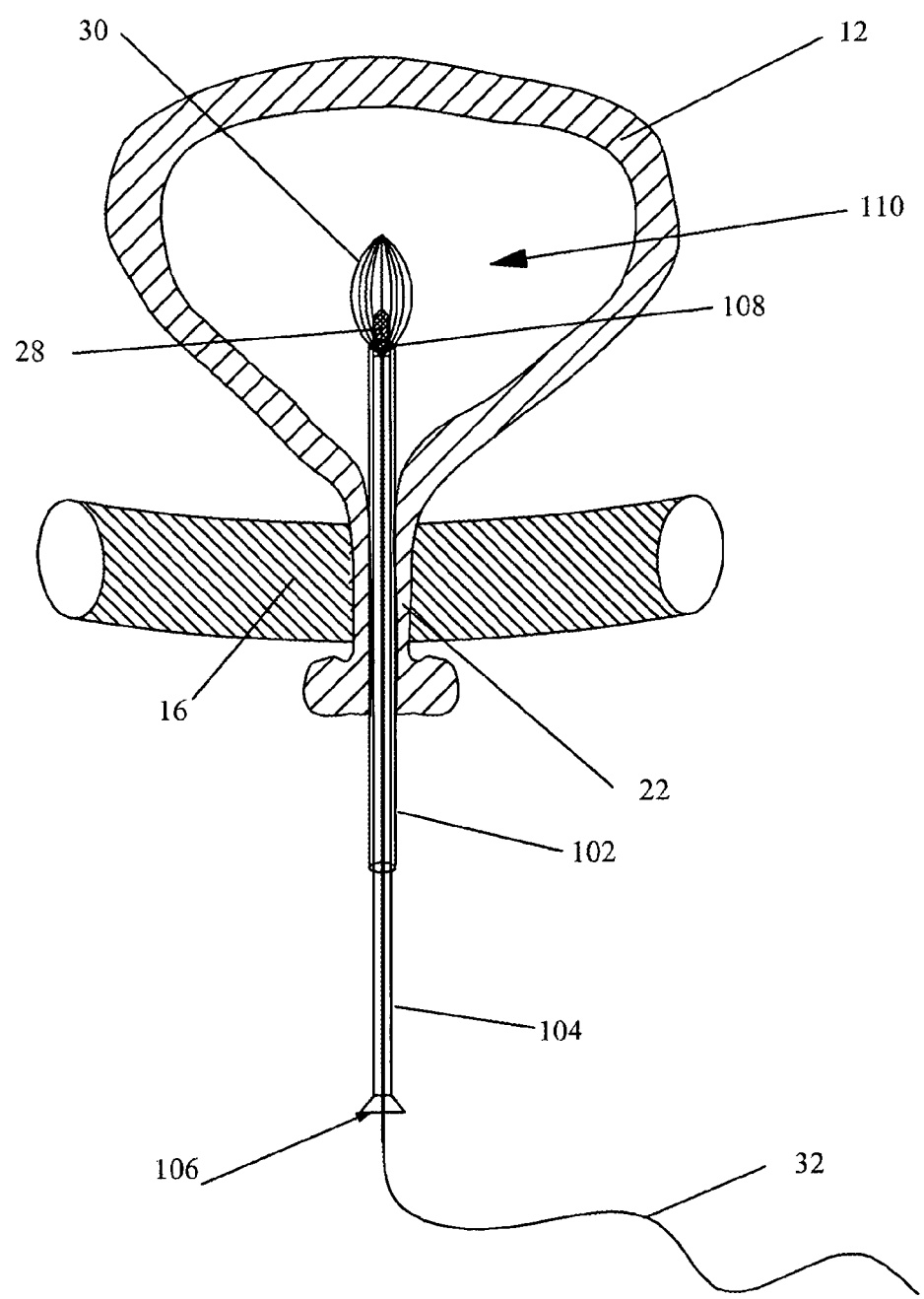

FIG. 9 illustrates the sensing device 28 being deposited 110 in the bladder 12. The distal tip 108 of the sheath 102 is within the bladder 12. The push rod 104 is then used to push the sensing device 28 out of the sheath 102.

Figure 10:
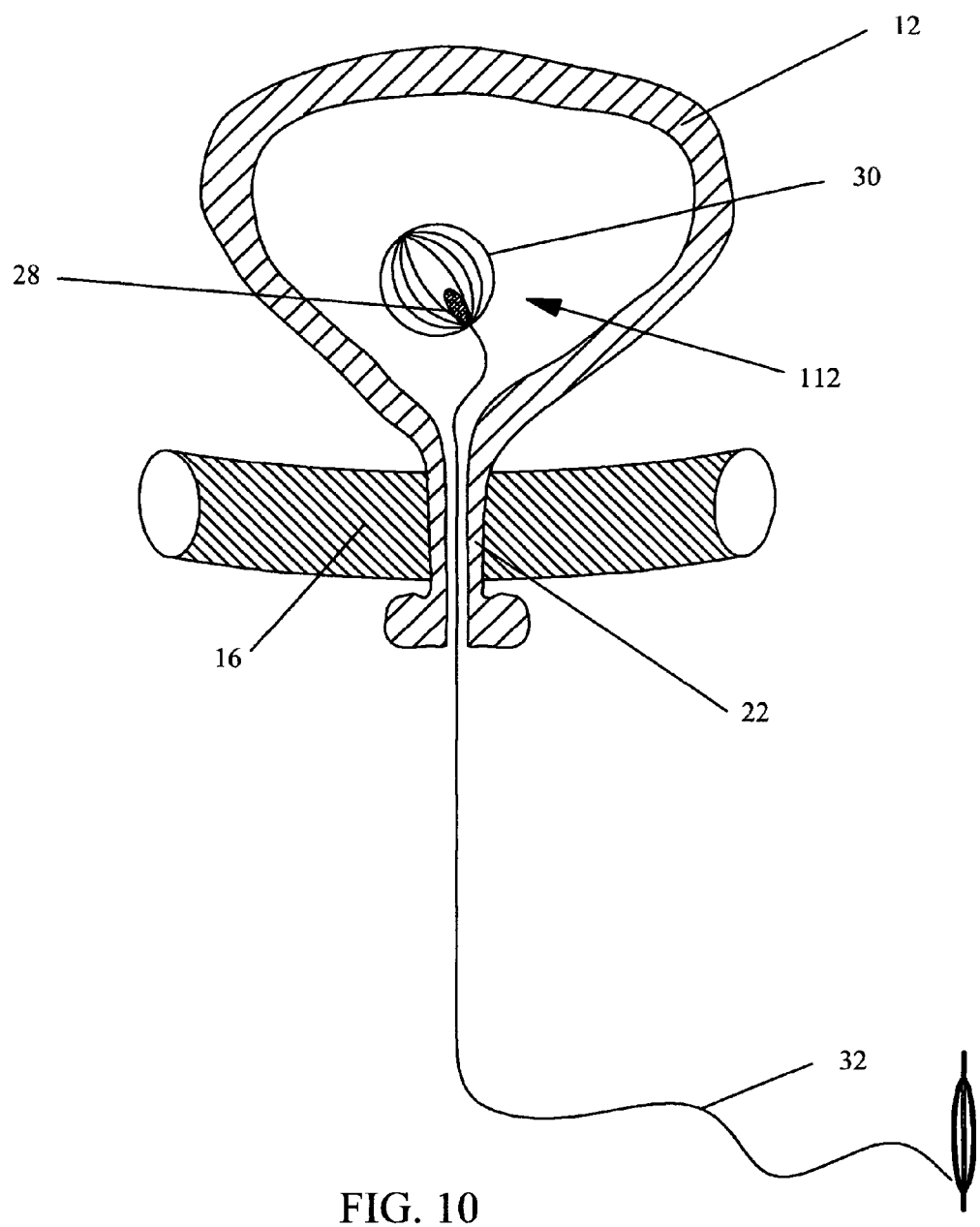

FIG. 10 illustrates the sensing device 28 after it has exited 112 the sheath 102 and the sheath 102 and the push rod 104 have been removed from the urethra 22. At this point, the housing 30 expands to a size that prevents the sensing device 28 from being ejected during voiding. The size of the housing 30 can be selected depending on the bladder capacity and urethral capacity of the patient (i.e., typically the diameter will be less than about 2 centimeters). The expanded size of the housing 30 is selected to minimize irritation to the bladder wall when the bladder is empty, and to prevent accidental ejection of the sensing device.

Removal of the sensing device enclosed within the housing consists of passing the retrieval wire through a new sheath. The sheath is then placed into the urethra and the sensing device is pulled into the opening of the sheath by the retrieval wire. The sensing device is then pulled completely into the sheath until it is fully enclosed by the sheath. The sensing device can then be safely removed from the bladder by withdrawing the sheath.

Figure 11:
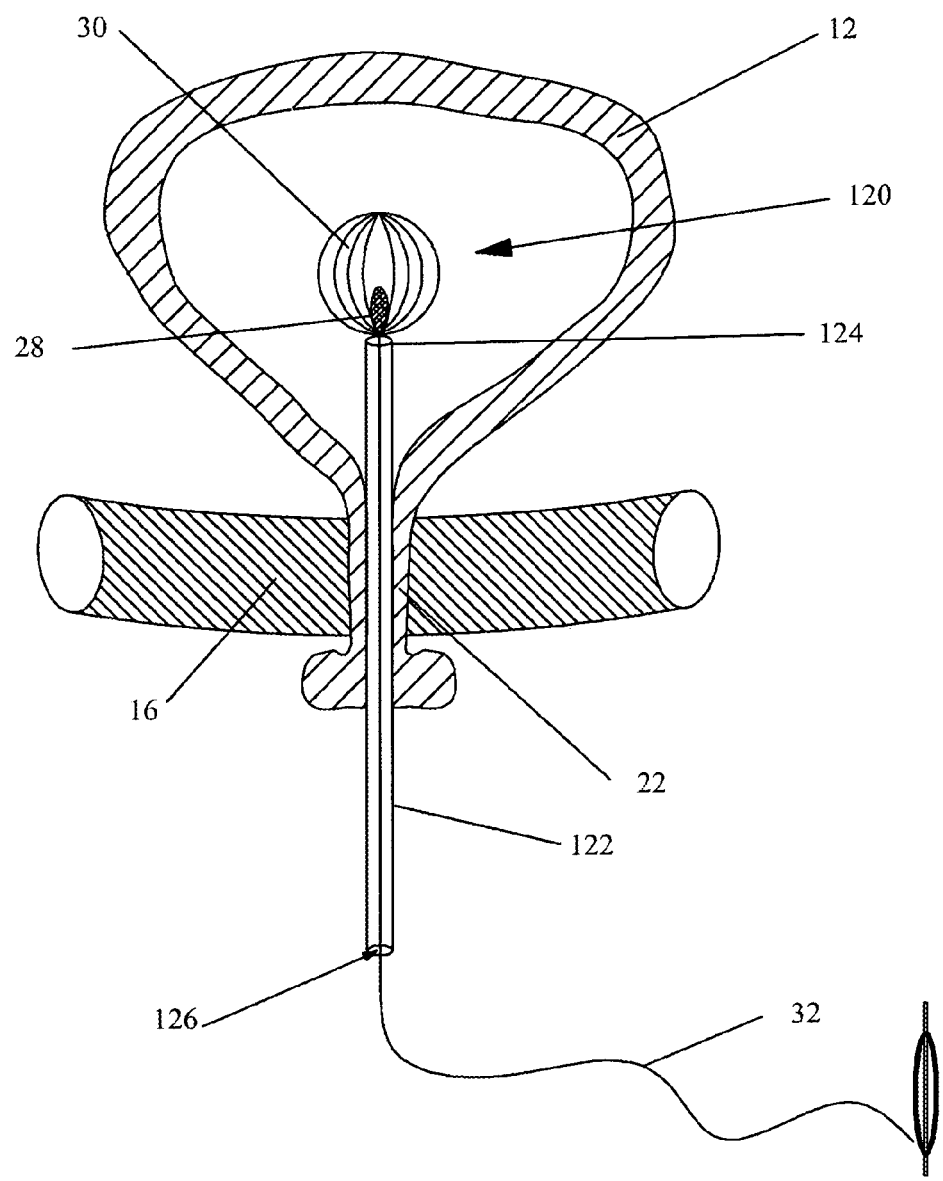
FIGS. 11 and 12 illustrate the retrieval of the sensing device from the bladder using a catheter.

FIG. 11 illustrates a first step 120 in the removal of the sensing device 28 enclosed within the housing 30 from the bladder 12. A new flexible sheath 122 is inserted into the urethra 22 and the distal tip 124 of the sheath 122 is positioned within the bladder 12. The retrieval wire 32 is initially fed through the lumen 126 of the new sheath 122. The user can easily detect, by tactile feedback, when the distal tip 124 of the new sheath 122 enters the bladder 12.

Figure 12:
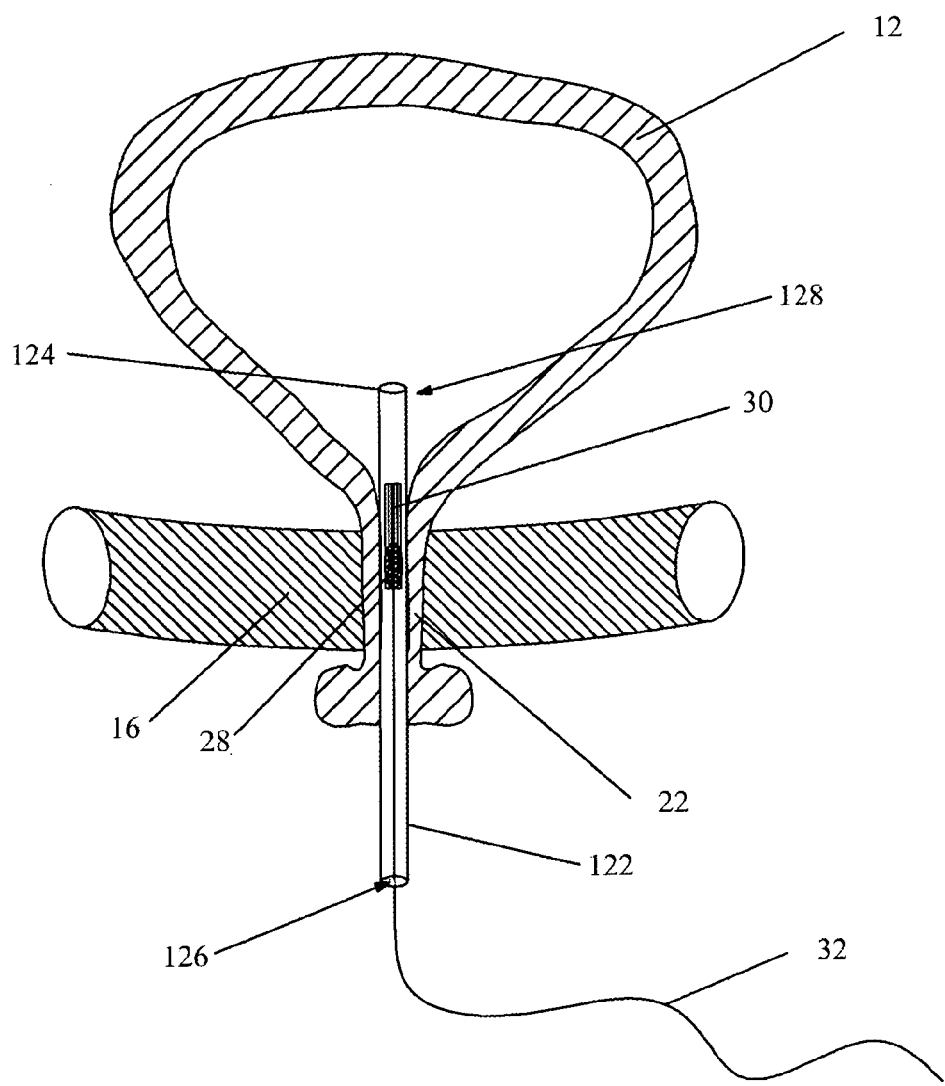

FIG. 12 illustrates the next step 128 in the removal of the sensing device 28 from the bladder 12. When then retrieval wire 32 is pulled, thereby collapsing the housing 30 and drawing the sensing device 28 into the distal tip 124 of the new sheath 120. At this point, the new sheath 120, housing the sensing device 28 and the housing 30, is removed completely from the bladder 12 and the patient.

In an alternative embodiment of the sheath (e.g., 102 and 122), optical fibers (not shown) are integrated into the wall of the sheath and are used to detect when the distal tip enters the bladder. An example of suitable optical technology is described in U.S. Pat. No. 5,303,026 to Bigio et al. When utilizing optical fibers integrated into the sheath, other properties of the tissue (e.g., blood volume, blood oxygenation, muscle thickness, and the like) can be measured.

The urinary diagnostic system can be used as a diagnostic tool in patients with urinary incontinence and abnormal voiding patterns. It can serve as a diagnostic tool by measuring dynamic pressures of the bladder during both the physiological filling and emptying phases of the bladder. The urinary diagnostic system is intended to measure the pressures of the bladder for up to 24 hours. During this time, bladder pressures can be evaluated over multiple cycles for detecting for abnormal patterns of the bladder. Points of incontinence can be correlated with the leak point pressures as well as bladder pressure patterns during voiding. Compliance can also be assessed with the bladder pressure profile.

Understanding the bladder pressure profile helps health care professionals plan more precise and therefore, effective treatment, for the patients. Some of the treatments include medications, pelvic exercises, biofeedback, and surgery. The bladder pressure profile can help to determine whether particular treatments would not be beneficial and may even be harmful. After different treatments, the bladder pressure profile can help to assess the results of the treatment and is an objective way to quantify treatment success or failure.

The present invention has several advantages. The first advantage is the present invention provides the user with privacy and comfort. One of the main barriers to treatment for those afflicted with urinary incontinence is the sheer embarrassment of presenting the problem to their health care professionals. Conventional diagnostic tools are inadequate and compound this problem since they are conducted in non-private clinical settings. In many doctors offices or similar situations, in order to monitor the situation and give proper instructions, a full diagnostic bladder pressure profile requires at least one attendant to be present in the room at all times while the bladder is being filled and even, in many cases, while the patient is trying to void. Many times, the best clinical leak point pressures (i.e., the pressure point at which the patient leaks urine) are measured with the patient in a standing position, instruments in place in the bladder, and/or vagina/rectum and with attendant(s) in the room for providing instructions. The patient is instructed to stand over towels or pads to catch any urinary leakage. It is a highly uncomfortable experience for many patients. This process may discourage some patients from seeking further diagnosis and, thus, treatment.

The present invention circumvents all of these problems, since once placed, our device is portable and wireless, thus, patients are clothed and able to be comfortable while the test is being conducted. Alarm features within the device can also provide the patient with biofeedback that can immediately help treat the problem.

A second advantage of the present invention is the wireless portability of the device. Because of its wireless portability, the present invention allows measurements of patients in many dynamic situations, such as standing, sitting, walking, jumping, and the like. This is important determination as many patients are continent, except under certain trigger situations. Identification of these trigger situations allows for better management and treatment plans for these patients. This is currently impossible using conventional practices.

Currently, patients are tethered to a machine in a single room. With the present invention, patients are able to move and be more comfortable. Thus, the degree of comfort allows for a more accurate bladder pressure profile to be obtained. Accuracy allows for better treatment planning.

Because of its portability, measurements can be made over multiple urinary cycles that would lend accuracy to the bladder pressure profile. The measurements can also be made overnight, a time when urinary incontinence is the most severe for many patients. Currently, conventional devices measure one single urinary cycle, fill and void. It has been impossible to measure any situation over night.

A third advantage of the present invention is the physiological filling and emptying of the bladder. All conventional devices for measuring bladder pressure profiles require the repeated filling of the bladder artificially by either instilling cold (or room temperature) saline into the bladder at a non-physiological pace (about 25 to about 50 cc/minute) or with an infusion of $CO_2$ gas to mimic the filling of the bladder in "fast time". Both these situations are not comparable to normal physiological filling of the bladder. The present invention is used while the bladder is filling under normal physiological conditions and with normal filling times. This is an important difference since nothing can artificially mimic the bladder's own pattern of filling and the present invention uses the bladder's own filling mechanism. This will result in a much more accurate bladder pressure profile.

A fourth advantage of the present invention is the administering of the diagnostic test. Conventional bladder pressure profile testing is labor intensive, needing highly skilled and trained technical staff in a specialized procedure room. The conventional testing is limited by the length of time needed per patient (i.e., normally about 1 hour), which can severely hinder the limited resources of a busy clinic. Only one patient can be tested at any one time with the conventional equipment. Using the present invention, placement of the sensing device can be completed by medical assistants in about a 5 to 10 minute clinical slot, needing no extra or special room. Multiple patients can be equipped with the device at any one time in different rooms and there is no limitation of room size or dependency on the equipment being currently in use. Removal of the sensing device from the bladder is also as easy, utilizing the same room with minimal staff. This is a major advantage of the present invention for efficient clinical use with significant economic savings of office space, staff training, equipment space, allotted clinical time, and patient comfort.

A fifth advantage of the present invention is improving the accuracy of results. Much of conventional bladder profile testing is administrator dependent. Since the present invention is a sensing device system, which receives and records the patient's data, independent of an administrator, it improves the accuracy of an appropriate clinical diagnosis.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for disposing and using a sensing device in a body part having an interior, the method comprising:
   disposing the sensing device having a retrieval wire into a deployable housing, said housing having a body defining an interior and an exterior, said housing configured to allow fluid to flow through said housing to the sensing device, wherein the sensing device is disposed in said interior of said housing;
   compressing said housing enclosing the sensing device into an interior of a first sheath;
   disposing a push bar into said interior of said first sheath proximate said housing;
   inserting said first sheath into the body part of a body;
   operating said push bar to dispose said housing enclosing the sensing device into the interior of the body part;
   removing said first sheath from the body part with said retrieval wire exiting the interior of the body part;
   collecting data using the sensing device;
   transmitting data from the sensing device to a remote processing device;
   locating said retrieval wire of the sensing device;
   inserting said retrieval wire of the sensing device through an interior of a second sheath;
   disposing said second sheath into the interior of the body part, said second sheath configured to receive said housing enclosing the sensing device;
   retracting said housing and the sensing device into said interior of said second sheath using said retrieval wire; and
   removing said second sheath from the body part.

2. The method of claim 1, wherein said sensing device is selected from the group consisting of pressure sensing devices, thermal sensing devices, conductive sensing devices, capacitive sensing devices, inductive sensing devices, resistive sensing devices, and optical pressure sensing devices.

3. The method of claim 1, wherein said processing device comprises an RF transceiver that is a passive transceiver.

4. The method of claim 1, wherein said retrieval wire is configured to operate as an antenna.

5. The method of claim 1, wherein said housing comprises a material selected from the group consisting of a polymer, polytetrafluoroethylene, non-dissolvable biocompatible materials, polyurethane, polyethylene, latex, titanium, copper, gold, surgical steel, polytetrafluoroethylene-coated metal, natural collagen, plain gut, polyglactin 910, polydioxanone, collagen, polyglyconate, and polyglycolic acid.

6. The method of claim 1, wherein said data is transmitted by radio frequency.

7. The method of claim 1, wherein said sensing device is accessible for retrieval from an exterior of a body.

8. The method of claim 1, further comprising:
   disposing a urine sensing device proximate said retrieval wire.

* * * * *